US008524289B2

(12) United States Patent
Shimizu et al.

(10) Patent No.: US 8,524,289 B2
(45) Date of Patent: Sep. 3, 2013

(54) PROCESS FOR PRODUCING CAROTENOID

(75) Inventors: Kentaro Shimizu, Shizuoka (JP);
Tomoyuki Ishizaki, Shizuoka (JP);
Toshiyuki Takahashi, Tokyo (JP);
Shotaro Uchizawa, Tokyo (JP)

(73) Assignee: JX Nippon Oil & Energy Corporation, Tokyo (JP)

( * ) Notice: Subject to any disclaimer, the term of this patent is extended or adjusted under 35 U.S.C. 154(b) by 84 days.

(21) Appl. No.: 13/203,324

(22) PCT Filed: Mar. 1, 2010

(86) PCT No.: PCT/JP2010/053245
§ 371 (c)(1),
(2), (4) Date: Sep. 20, 2011

(87) PCT Pub. No.: WO2010/098484
PCT Pub. Date: Sep. 2, 2010

(65) Prior Publication Data
US 2012/0004319 A1    Jan. 5, 2012

(30) Foreign Application Priority Data
Feb. 27, 2009    (JP) .................. 2009-046105

(51) Int. Cl.
*A01N 65/00*    (2009.01)
(52) U.S. Cl.
USPC ....................................... 424/725
(58) Field of Classification Search
None
See application file for complete search history.

(56) References Cited

U.S. PATENT DOCUMENTS

| 4,522,743 A | 6/1985 | Horn et al. |
| 5,591,343 A | 1/1997 | Kitaoka et al. |
| 5,858,761 A | 1/1999 | Tsubokura et al. |
| 2004/0115758 A1 | 6/2004 | Shimada et al. |
| 2007/0105189 A1 | 5/2007 | Tsubokura et al. |

FOREIGN PATENT DOCUMENTS

| EP | 0670306 A1 | 9/1905 |
| EP | 0732378 A2 | 9/1996 |
| EP | 2017262 A1 | 1/2009 |
| JP | 57-195161 A | 11/1982 |
| JP | 7-79796 A | 3/1995 |
| JP | 7-242821 A | 9/1995 |
| JP | 8-89280 A | 4/1996 |
| JP | 8-258595 A | 10/1996 |
| JP | 10-276721 A | 10/1998 |
| JP | 11-56346 A | 3/1999 |
| JP | 2002-218994 A | 8/2002 |
| JP | 2004-41147 A | 2/2004 |
| JP | 2004-208504 A | 7/2004 |
| JP | 2005-87099 A | 4/2005 |
| JP | 2007-244205 A | 9/2007 |
| JP | 2007-261972 A | 10/2007 |
| JP | 2007-319015 A | 12/2007 |

*Primary Examiner* — Michael Meller
(74) *Attorney, Agent, or Firm* — McDermott Will & Emery LLP

(57) ABSTRACT

The present invention provides a method for producing a carotenoid-containing composition, comprising the steps of: subjecting a culture of a carotenoid-producing microorganism to an extraction treatment using a water-soluble organic solvent; dispersing the resulting extract solution in water for micellization; heat stirring the resulting micellized solution in a solvent break the micelles and precipitate the carotenoid component of interest to obtain the precipitate; collecting and heat washing the precipitate with ethanol; and further subjecting the precipitate to pulverization/drying; and food, a pharmaceutical composition and a cosmetic product comprising the carotenoid-containing composition.

9 Claims, No Drawings

SEQUENCE LISTING

```
<160> NUMBER OF SEQ ID NOS: 1

<210> SEQ ID NO 1
<211> LENGTH: 1452
<212> TYPE: DNA
<213> ORGANISM: Unknown
<220> FEATURE:
<223> OTHER INFORMATION: Description of Unknown Organism:E-396
<220> FEATURE:
<221> NAME/KEY: misc_feature
<222> LOCATION: (1350)..(1350)
<223> OTHER INFORMATION: n is a, c, g, or t

<400> SEQUENCE: 1
```

-continued

```
agtttgatcc tggctcagaa cgaacgctgg cggcaggctt aacacatgca agtcgagcga      60
gaccttcggg tctagcggcg gacgggtgag taacgcgtgg gaacgtgccc ttctctacgg     120
aatagccccg ggaaactggg agtaataccg tatacgccct ttgggggaaa gatttatcgg     180
agaaggatcg gcccgcgttg gattaggtag ttggtggggt aatggcccac caagccgacg     240
atccatagct ggtttgagag gatgatcagc cacactggga ctgagacacg gcccagactc     300
ctacgggagg cagcagtggg gaatcttaga caatggggggc aaccctgatc tagccatgcc    360
gcgtgagtga tgaaggcctt agggttgtaa agctctttca gctgggaaga taatgacggt     420
accagcagaa gaagccccgg ctaactccgt gccagcagcc gcggtaatac ggagggggct     480
agcgttgttc ggaattactg ggcgtaaagc gcacgtaggc ggactggaaa gtcagaggtg     540
aaatcccagg gctcaacctt ggaactgcct ttgaaactat cagtctggag ttcgagagag     600
gtgagtggaa ttccgagtgt agaggtgaaa ttcgtagata ttcggaggaa caccagtggc     660
gaaggcggct cactggctcg atactgacgc tgaggtgcga aagcgtgggg agcaaacagg     720
attagatacc ctggtagtcc acgccgtaaa cgatgaatgc cagacgtcgg caagcatgct     780
tgtcggtgtc acacctaacg gattaagcat tccgcctggg gagtacggtc gcaagattaa    840
aactcaaagg aattgacggg ggcccgcaca agcggtggag catgtggttt aattcgaagc    900
aacgcgcaga accttaccaa cccttgacat ggcaggaccg ctggagagat tcagctttct    960
cgtaagagac ctgcacacag gtgctgcatg gctgtcgtca gctcgtgtcg tgagatgttc   1020
ggttaagtcc ggcaacgagc gcaacccacg tccctagttg ccagcaattc agttgggaac   1080
tctatggaaa ctgccgatga taagtcggag gaaggtgtgg atgacgtcaa gtcctcatgg   1140
gccttacggg ttgggctaca cacgtgctac aatggtggtg acagtgggtt aatccccaaa   1200
agccatctca gttcggattg tcctctgcaa ctcgagggca tgaagttgga atcgctagta   1260
atcgcggaac agcatgccgc ggtgaatacg ttcccgggcc ttgtacacac cgcccgtcac   1320
accatgggag ttggttctac ccgacgacgn tgcgctaacc ttcgggggggc aggcggccac   1380
ggtaggatca gcgactgggg tgaagtcgta acaaggtagc cgtaggggaa cctgcggctg   1440
gatcacctcc tt                                                        1452
```

PROCESS FOR PRODUCING CAROTENOID

CROSS REFERENCE TO PRIOR APPLICATIONS

This application is a U.S. National Phase application under 35 U.S.C. §371 of International Application No. PCT/JP2010/053245, filed on Mar. 1, 2010 and claims benefit of priority to Japanese Patent Application No. 2009-046105, filed on Feb. 27, 2009. The International Application was published in Japanese on Sep. 2, 2010 as WO 2010/098484 A1 under PCT Article 21(2). All of these applications are herein incorporated by reference.

FIELD OF THE INVENTION

The present invention relates to a method for producing a carotenoid, and in particular to an industrially suitable method for producing astaxanthin usable as a component of food, pharmaceutical compositions or cosmetic products. Specifically, the present invention relates to a purification treatment method comprising dispersing a solution of a culture of a carotenoid-producing microorganism extracted with a water-soluble organic solvent in water for micellization, and subsequently breaking the micelles by heat stirring at an appropriate solvent concentration for appropriate time, thereby preferentially crystallizing/precipitating a carotenoid component of interest. The present invention is further characterized by heat washing the precipitate obtained by the above-described purification treatment with ethanol, and subsequently subjecting the resultant to pulverization/drying. The present invention also relates to a method for producing a composition characterized by using only ethanol as an organic solvent, wherein the composition has a carotenoid content of 85% or higher, astaxanthin of 40% or higher in the carotenoid, a ratio of canthaxanthin to astaxanthin of 2.5% or lower, a ratio of cis-astaxanthin to trans-astaxanthin of 20% or lower or an ethanol content of 200 ppm or less, or wherein the composition has any combination features of the above-mentioned features. The present invention also relates to a carotenoid-containing composition obtained by the above-mentioned method; and further to food, a pharmaceutical composition or a cosmetic product comprising such a carotenoid-containing a composition.

BACKGROUND OF THE INVENTION

Carotenoids are natural pigments widely existent in the natural world, and are polyene pigments having a color in the range of yellow to red or purple. Astaxanthin is one type of naturally-occurring carotenoids and exists in a free state or as an ester, or exists as various types of pigment proteins by bonding with proteins.

Astaxanthin is widely used as a coloring agent for fishes and chicken's eggs. Astaxanthin is also approved as a food additive and is widely used in fat and oil processed foods, protein foods, aqueous liquid foods and the like. Astaxanthin also has an anti-oxidation activity against peroxidation of a lipid induced by a free radical, a singlet oxygen quenching action which can be more effective by several hundred times than that of $\alpha$-tocopherol or the like, and therefore is expected to be used as functional foods, cosmetic products and pharmaceutical drugs utilizing the strong anti-oxidation activity thereof.

Astaxanthin is distributed widely in the natural world in, for example, fishes such as salmon, trout and red sea bream; and crustaceans such as crab, shrimp and krill. Astaxanthin is also produced by bacteria belonging to genera *Agrobacterium, Brevibacterium* and *Paracoccus* as well as and microorganisms including *Haematococcus* green algae, *Phaffia* a yeasts and the like. Carotenoids such as astaxanthin, zeaxanthin or the like are industrially produced by a chemical synthesis method, however carotenoids derived from natural products are desired from a safety perspective.

In view of such a background, many methods for producing carotenoids containing astaxanthin derived from algae or microorganisms which are considered to be suitable for mass production have been reported.

For example, the following method for producing a carotenoid from a *Haematococcus* alga has been reported (Patent Document 1). A cystocyte of a cultured alga is treated with heated acetone to elute chlorophyll, i.e., a contaminant. Then, the cystocyte is spray-dried, and a carotenoid is extracted from the resultant dry cells with ethanol. However, a composition obtained by such a method still contains many contaminants from the organisms, and is not satisfactory in terms of 1) the carotenoid content, 2) the astaxanthin content, and the like.

In order to obtain a composition containing astaxanthin at a high content, the following method has been reported (Patent Document 2). A crude xanthophylls obtained according to the above-described method is allowed to react with lipase in the presence of water to decompose a neutral lipid, i.e., one of the contaminants, thereby separating the lipase enzyme-treated liquid into oil and water. From the separated oil layer, free fatty acid is separated from astaxanthin by distillation, whereby the astaxanthin is concentrated a purified. However, even after such complicated treating steps, a composition with an astaxanthin content of 30% or higher has not been obtained.

A method of obtaining astaxanthin contained at a ratio of 0.5 to 60% using a supercritical fluid extraction method (Patent Document 3) has also been reported. However, an astaxanthin fraction of a content less than the targeted content is produced as a sub-product during this treatment and discarded, or in order to increase the astaxanthin content of such a fraction, another concentration operation is required. Therefore, this production method is again not satisfactory, in terms of simplicity and cost, as an industrial method for producing a highly pure carotenoid containing a high content of astaxanthin with little contaminants derived from organisms.

As a method using *Phaffia* yeast, the following method has been reported (Patent Document 4). A fractured bacterial body of the yeast is treated with extraction using an organic solvent, and the oil-like crude extract obtained by concentrating the extract solution is purified by ion exchange chromatography, adsorption chromatography or the like to obtain astaxanthin. However, this method employs a plurality of column chromatographies to purify a crude solution having lower concentration astaxanthin and thus is difficult to be used for industrial application.

As another method, the following method has also been reported (Patent Document 5). A bacterial body obtained, by culturing *Phaffia* yeast is treated with extraction using acetone, and the resultant extract is concentrated to obtain a crude extract. A hydrocarbon-based solvent is added to this crude extract for crystallization. This method is highly simple, but the obtained composition contains a carotenoid at a content of about 70 to 73% (36 to 42% in terms of astaxanthin content). Accordingly, this method is not satisfactory as a method for producing a highly pure carotenoid with a small amount of contaminants derived from organisms. In addition, this method is also not satisfactory for the reason that there is a concern that acetone and the hydrocarbon-based solvent may remain in the carotenoid.

As methods using E-396 strain (FERM BP-4283: deposited on Apr. 27, 1993 (date of original deposition), International Patent Organism Depositary, National Institute of Advanced Industrial Science and Technology (Central 6, Higashi 1-1-1, Tsukuba-shi, Ibaraki-ken, Japan)), a bacterium that can produce astaxanthin, adonixanthin and the like, the following methods have been reported: a method employing extraction treatment by contacting an organic cyclic hydrophilic compound, which invokes a safety concern regarding the use in food production, with the bacterial body (Patent Document 6); a method employing supercritical fluid extraction like Patent Document 3 (Patent Document 7); a method employing liquid-liquid extraction by contacting the bacterial body with a water-soluble organic solvent, a nonpolar solvent and water (Patent Document 8); and a method employing extract on by contacting E-396 strain with a water-soluble organic solvent for concentration/crystallization and the washing the crystal with a solvent (Patent Document 9).

Under these circumstances, a method for industrially producing a highly pure carotenoid containing astaxanthin at a high content by a simple way without requiring any special facilities is strongly desired to be established.

RELATED ART DOCUMENTS

Patent Documents

Patent Document 1: Japanese Laid-Open Patent Publication No. H 11-56346
Patent Document 2: Japanese Laid-Open Patent Publication No. 2002-218994
Patent Document 3: Japanese Laid-Open Patent Publication No. 2004-41147
Patent Document 4: Japanese Laid-Open Patent Publication No. H 10-276721
Patent Document 5: Japanese Laid-Open Patent Publication No. 2004-208504
Patent Document 6: Japanese Laid-Open Patent Publication No. H 7-242621
Patent Document 7: Japanese Laid-Open Patent Publication No. H 8-89280
Patent Document 8: Japanese Laid-Open Patent Publication No. H 8-253695
Patent Document 9: Japanese Patent Application No. 2006-087223

SUMMARY OF THE INVENTION

Problems to be Solved by the Invention

The present invention has objectives of providing a composition containing a highly pure carotenoid at a high content with a lower canthaxanthin content which has a concern of excess intake upon high consumption, using only a safe solvent with a lower solvent residual level, a method for industrially producing the same, and further functional food, a pharmaceutical composition and a cosmetic product comprising such a composition.

Means for Solving the Problems

In order to solve the above problems, the present inventors have conducted studies focusing on microorganism culture and newly found the following problems of the conventional liquid-liquid extraction techniques and methods comprising extraction with a water-soluble organic solvent for concentration/crystallization and washing the crystal: 1) the ratio of canthaxanthin and astaxanthin does not change before and after the purification procedure and thus canthaxanthin contained in the resulting carotenoid-containing composition cannot be reduced; and 2) a large amount, i.e., 1% or higher, of residual solvent is contained in the bulk and it is difficult to reduce the residual solvent to an acceptable level in terms of functionality evaluation even by repeating pulverization/drying. As a result of further keen studies including solutions for these problems, the present inventors found that a highly pure carotenoid composition with less canthaxanthin content and less residual solvent can be obtained by: dispersing an extract solution obtained by subjecting a culture of a carotenoid-producing microorganism to extraction with a water-soluble organic solvent in water for micellization; heat stirring at an appropriate solvent concentration for appropriate time to break the micelles; preferentially crystallizing/precipitating astaxanthin to reduce canthaxanthin contained in the resulting carotenoid-containing composition; heat washing the precipitate with ethanol; and then subjecting the resultant to pulverization/drying, thereby accomplishing the present invention.

Thus, the present invention has the following constitution.

(1) A method for purifying a carotenoid, comprising the following steps 1) to 3):
 1) subjecting a culture of a carotenoid-producing microorganism to an extraction treatment using a water-soluble organic solvent;
 2) dispersing the resulting extract solution in water for micellization; and
 3) heat stirring the resulting micellized solution in a solvent to break the micelles and precipitate the carotenoid component of interest.

(2) A method for producing a carotenoid-containing composition, comprising the following steps 1) to 5):
 1) subjecting a culture of a carotenoid-producing microorganism to an extraction treatment using a water-soluble organic solvent;
 2) dispersing the resulting extract solution in water for micellization;
 3) heat stirring the resulting micellized solution in a solvent to break the micelles and precipitate the carotenoid component of interest to obtain the precipitate;
 4) collecting and heat washing the precipitate with ethanol; and
 5) further subjecting the precipitate to pulverization/drying.

(3) The method according to (1) or (2) above wherein the water-soluble organic solvent is ethanol.
(4) The method according to any one of (1)-(3) above wherein the carotenoid component of interest is astaxanthin.
(5) The method according to any one of (1)-(4) above wherein the carotenoid-containing composition is a composition containing a carotenoid for 85% or higher.
(6) The method according to any one of (1)-(5) above wherein a ratio of astaxanthin to the carotenoid contained in the carotenoid-containing composition is 40% or higher.
(7) The method according to any one of (1)-(6) above wherein a ratio of canthaxanthin to astaxanthin contained in the carotenoid-containing composition is 2.5% or lower.
(8) The method according to any one of (1)-(7) above wherein a ratio of cis-astaxanthin to trans-astaxanthin contained in the carotenoid-containing composition is 20% or lower.
(9) The method according to any one of (1)-(8) above wherein the ethanol content in the carotenoid-containing composition is 200 ppm or less.

(10) The method according to any one of (1)-(9) above wherein the microorganism is a bacterium that belongs to genus *Paracoccus*.
(11) The method according to any one of (1)-(10) above wherein a base sequence of DNA corresponding to 16S ribosome RNA of the microorganism is substantially homologous with the base sequence represented by SEQ ID NO: 1.
(12) The method according to any one of (1)411) above wherein the microorganism is E-396 strain (FERM BP-4283) or a mutant strain thereof.
(13) A carotenoid-containing composition obtained by the method according to any one of (1)-(12) above.
(14) The carotenoid-containing composition according to (13) above wherein the carotenoid is in a free form.
(15) Food, a pharmaceutical composition or a cosmetic product comprising the carotenoid-containing composition according to (13) or (14) above.

Effect of the Invention

The present invention can provide a composition containing, at a high content, a highly pure and safe carotenoid derived from natural products; a method for industrially producing the same; and further functional food, a pharmaceutical composition and a cosmetic product comprising such a composition.

The acceptable intake of canthaxanthin is regulated to 0.025 mg/kg/day, which has been associated with undesirable likelihood that one could exceed the regulated level upon an excess intake of a carotenoid-containing substance. In a carotenoid-containing composition of the present invention, a ratio of a carotenoid component of interest (for example, astaxanthin) can selectively be increased so as to lower the content percentage of an undesirable carotenoid component (for example, canthaxanthin).

EMBODIMENTS FOR CARRYING OUT THE INVENTION

Hereinafter, the present invention will be specifically described. The scope of the present invention should not be restricted by the description, and, besides the following examples, the invention may appropriately be modified without departing from the spirit of the present invention.

All the publications cited herein, for example, related art documents, laid-open patent applications, patent publications and other patent documents, are incorporated herein in their entirety by reference. The present specification incorporates the contents of the specification of Japanese Patent Application No. 2009-046105 (filed on Feb. 27, 2009), based on which the present application claims the benefit of priority.

Microorganisms that can be used for the present invention are not limited at all as long as they can produce a carotenoid while *Paracoccus* bacteria, *Haematococcus* algae, *Phaffia* yeasts or the like can be used. Examples of *Paracoccus* bacteria include *Paracoccus carotinifaciens, Paracoccus marcusii, Paracoccus haeundaensis, Paracoccus zeaxanthinifaciens, Paracoccus denitrificans, Paracoccus aminovorans, Paracoccus aminophilus, Paracoccus kourii, Paracoccus halodenitrificans* and *Paracoccus alcaliphilus*. Examples of Haematococcus algae include *Haematococcus pluvialis, Haematococcus lacustris, Haematococcus capensis, Haematococcus droebakensis* and *Haematococcus zimbabwiensis*. An example of *Phaffia* yeasts includes *Phaffia rhodozyma*. However, microorganisms used for the present invention are not limited to these examples.

Bacteria belonging to genus *Paracoccus* are particularly preferable in terms of the speed of proliferation rate and productivity of carotenoids. Preferably, the carotenoid-producing bacteria are bacteria whose base sequences of DNA corresponding to 16S ribosome RNA are substantially homogenous with the base sequence of E-396 strain represented by SEQ ID NO: 1. The phrase "substantially homologous" means that the sequence represented by SEQ ID NO:1 and a sequence to be compared have homology of 95% or higher, preferably 96% or higher, and more preferably 98% or higher, in consideration of the error frequency in sequencing DNA. Among such bacteria, *Paracoccus carotinifaciens* E-396 strain (FERM BP-4283) is especially preferable. It is also very preferable to mutate these microorganisms and select a strain that is highly productive of a carotenoid for the purpose of improving the carotenoid productivity.

There is no specific limitation to the method for producing a mutant as long as the method induces mutation. Usable methods include, for example, a chemical method using a mutating agent such as N-methyl-N'-nitro-N-nitrosoguanidine (NTG), ethylmethanesulfonate (EMS) or the like; a physical method using ultraviolet radiation, x-ray radiation or the like; or a biological method using gene recombination, transposon or the like. The mutation process may be performed once, or twice or more where, for example, a mutant of an astaxanthin-producing microorganism is obtained by the above mutation process and then the obtained mutant is further subjected to another mutation process.

A culture of a carotenoid-producing microorganism usable for the present invention is not limited as long as it is a culture obtained by a method capable of efficiently culturing the above-described microorganism, for example, a method utilizing a liquid culture, a solid culture or a combination thereof using any of the following media. As used herein, the term "culture" refers to any one of culture supernatant, a cultured bacterial body and a fractured bacterial body product.

A nutrition medium usable for culturing a microorganism used for the present invention is sufficient as long as it is a nutrition medium containing a carbon source, a nitrogen source and an inorganic salt necessary for growing a production bacterium. It may be more preferable to add a vitamin. It may be preferable to further add amino acid, nucleic acid base or the like. Other substances which may optionally be added include yeast extract, peptone, meat extract, malt extract, corn steep liquor, dry yeast, soybean cake and the like.

Usable carbon sources include sugars such as glucose, sucrose, lactose, fructose, trehalose, mannose, mannitol, maltose and the like; organic acids such as acetic acid, fumaric acid, citric acid, propionic acid, malic acid, malonic acid, pyruvic acid and the like; alcohols such as ethanol, propanol, butanol, pentanol, hexanol, isobutanol, glycerol and the like; fats and oils such as soybean oil, rice bran oil, olive oil, corn oil, sesame oil, linseed oil and the like; etc. These carbon sources may be used alone or in combination two or more. The ratio for addition depends on the type of the carbon source and may be appropriately adjusted, but it is usually 1 to 100 g and preferably 2 to 50 g per 1 L of the medium.

Usable nitrogen sources include, for example, potassium nitrate, ammonium nitrate, ammonium sulfate, ammonium chloride, ammonium phosphate, ammonia, urea and the like where these nitrogen sources may be used alone or in a combination of two or more. The ratio for addition depends on the type of the nitrogen source and may be appropriately adjusted, but it is usually 0.1 to 30 g and preferably 1 to 10 g per 1 L of the medium.

Usable inorganic salts include potassium dihydrogen phosphate, dipotassium hydrogen phosphate, disodium hydrogen phosphate, magnesium sulfate, magnesium chloride, iron sulfate, iron chloride, manganese sulfate, manganese chloride, zinc sulfate, lead chloride, copper sulfate, calcium chloride, calcium carbonate, sodium carbonate, and the like where these inorganic salts may be used alone or in a combination of two or more. The ratio for addition depends on the type of the inorganic salt and may be appropriately adjusted, but it is usually 0.001 to 10 g per 1 L of the medium.

When a vitamin is added, the amount added depends on the type of the vitamin and may be appropriately adjusted, but it is usually 0.1 to 1000 mg and preferably 1 to 100 mg per 1 L of the medium.

The added amount of amino acid, nucleic acid base, yeast extract, peptone, meat extract, malt extract, corn steep liquor, dry yeast, soybean cake and the like depends on the type of the substance and may be appropriately adjusted, but it is usually 0.2 g to 200 g and preferably 3 to 100 g per 1 L of the medium.

The pH of the medium is adjusted to 2 to 12, preferably 6 to 9. The culture conditions are set to a temperature of 15 to 80° C., preferably 20 to 35° C. for 1 to 20 days, preferably 2 to 8 days, under an aerobic condition. The aerobic condition includes, for example, shaking culture, aeration and stirring culture, or the like.

According to a more preferable example of a method for extracting astaxanthin produced by a cultured microorganism used for the present invention, the culture solution or a bacterial body concentrate, a wet bacterial body or a dry bacterial body obtained from the culture solution is subjected to the following extraction treatment after the cultivation. The above-mentioned concentrate of a bacterial body may be obtained, for example, by subjecting the culture solution to concentration by membrane filtration while the above-mentioned wet bacterial body may be obtained by subjecting the culture solution to a generally known filtration process such as centrifugation, filtration under pressure or filtration under reduced pressure. Furthermore, the wet bacterial body may be dried by a generally known drying process such as spray drying, fluidized drying, rotating drum drying or lyophilization to obtain a dry bacterial body. In addition, at the stage of the culture solution, the bacterial body concentrate, the wet bacterial body or the dry bacterial body prior to the following extraction, one or more treatments among a chemical treatment using an alkaline reagent, a surfactant or the like, a biochemical treatment using a bacteriolytic enzyme, a lipid degrading enzyme, a proteolytic enzyme or the like, and a physical treatment using ultrasonic waves, pulverization or the like may be performed alone or in combination. In the case of the dry bacterial body about 10-30 mg of astaxanthin and about 0.3-1.2 mg of canthaxanthin per gram of the bacterial body are considered to be contained.

Examples of the water-soluble organic solvents used for extraction according to the present invention include ethanol, acetone, methanol, n-propanol, isopropanol, methylethyl ketone, diethyl ketone and tetrahydrofuran, while ethanol or acetone is preferably used and ethanol is particularly preferably used. Moreover, two or more of these water-soluble organic solvents may be mixed together for use. The temperature of ethanol upon extraction is preferably 80° C. or higher, more preferably 85° C. or higher, still more preferably 90° C. or higher and particularly preferably 93° C. or higher. The temperature upon extraction relates to, the increase of solubility of carotenoid including astaxanthin in ethanol, and is important for increasing the extraction efficiency. The upper limit temperature of ethanol upon extraction is preferably 150° C. or lower, more preferably 130° C. or lower, still more preferably 120° C. or lower and particularly preferably 110° C. or lower. This upper limit temperature is important for suppressing thermal degradation of the carotenoid including astaxanthin. Since the extraction procedure requires the temperature of the solvent to be at the boiling point or higher, the treatment needs to be performed in a closed-type pressure vessel. In this case, the treatment should be performed at the gauge pressure of up to 0.8 MPa or lower, and preferably 0.4 MPa or lower.

The amount of ethanol is defined according to the temperature upon extraction, any amount is possible as long as it can dissolve the amount of astaxanthin contained in the bacterial bodies. In the case of extraction from a dry bacterial body using ethanol, the amount of ethanol is 300-3,000 g, preferably 500-2,000 g, and more preferably 800-1,600 g per gram of astaxanthin contained in the bacterial bodies.

For example, where the extraction is performed on 1 g of dry bacterial bodies containing about 20 mg of astaxanthin by using ethanol at 95° C., ethanol of about 10-35 g is preferably used.

Extraction may be performed with hydrous ethanol such as ethanol collected from an aqueous ethanol solution by distillation. The amount of water is not particularly limited, but it is preferably 10% or lower. In the case of extraction with hydrous ethanol, solubility of the carotenoid including astaxanthin becomes lower than the case of extraction with anhydrous ethanol. Therefore, the extraction temperature is set higher for better extraction efficiency.

In order to prevent oxidation of a carotenoid upon extraction procedure as much as possible, a treatment can be performed in an inert gas atmosphere such as nitrogen gas, or an antioxidant used for pharmaceutical products or food is selected and added to the extraction solvent for the extraction procedure. Alternatively, these treatments may be combined together.

The above-mentioned antioxidant is preferably removed from the carotenoid composition at the end but the antioxidant may not necessary be removed depending on the type used (for example, vitamin C).

Moreover, in order to prevent degradation of a carotenoid due to light as much as possible, the extraction procedure may be carried out under lightless conditions.

The extraction time is not necessarily limited, but it is preferably short to minimize reduction in the yield caused by thermal degradation, and it is preferably within 60 minutes, and more preferably within 30 minutes.

A method for separating the extract solution resulting from the extraction procedure from the microorganism is not particularly limited. For example, membrane filtration, centrifugation, decantation or the like may be employed while centrifugation is preferable for industrial use. The temperature for separation is not particularly limited for industrial purpose. Once a carotenoid pigment is extracted at a high temperature of 93° C. or higher and dissolved in a lower alcohol, it does not easily be precipitated in a short time even when it is cooled to −20° C.-70° C. Thus, the extract solution can be stably separated even at a lower temperature.

In order to disperse the extract solution in water for micellization, for example, a method may be employed in which the extract solution is added using an injector or a pump while strongly stirring the water with a stir bar or a stir blade. The temperature of the water used for dispersion is not particularly limited but it is preferably 5° C. or higher, more preferably 30° C. or higher, still more preferably 50° C. or higher and particularly preferably 60° C. or higher. The upper limit temperature of the water is preferably 100° C., i.e., the boiling point of water, or less, more preferably 85° C. or lower and still more preferably 70° C. or lower. The volume ratio of water and the added extract solution is 100:100 to 100:5, preferably 100:50 to 100:10 and more preferably 100:35 to 100:15. The time required for addition may be determined to a rate that allows effortless dispersion in consideration of the mixing capacity of the stirring device. Since precipitation takes place as the solvent concentration becomes higher as will be described later, the time for addition is better be short in order to maintain constant precipitation time, and it is preferably within 30 minutes and more preferably within 10 minutes.

The preferential crystallization/precipitation of astaxanthin according to the method of the present invention may be accomplished by heat stirring to break the micelles while maintaining the concentration of the solvent in the micellized solution. The term "preferential" means that the carotenoid component of interest (for example, astaxanthin) is contained in the carotenoid-containing composition of the present invention obtained by crystallization/precipitation at a high ratio relative to the raw precipitate solution. As to the precipitation speed with respect to a concentration of each component con tamed in the carotenoid composition, since the precipitation speed of astaxanthin is faster than that of canthaxanthin, the carotenoid composition in the precipitate contains more astaxanthin and less canthaxanthin as compared to the ratio of astaxanthin and canthaxanthin in the raw precipitate solution micellized solution). As a result, canthaxanthin contained in the resulting carotenoid composition can be reduced.

As the precipitation proceeds, the precipitation speed of astaxanthin gradually becomes slower while the precipitation speed of canthaxanthin does not become so slow. Accordingly, the amount of precipitated canthaxanthin will gradually increase with time, and the ratio of canthaxanthin will come close to the composition of the raw precipitate solution (micellized solution). Therefore, precipitation should be terminated at a desirable point and proceed to separation/collection of the precipitate as will be described later.

The concentration of the solvent maintained in the micellized solution influences the precipitation speed where the higher the concentration is, the faster the precipitation speed will become. In the case of ethanol, increase in the concentration by 1% increases the precipitation speed for about 1.7 times. Meanwhile, change in the ethanol concentration does not change the carotenoid content in the resulting precipitate and thus does not affect the quality. As described above, as the precipitation proceeds and the astaxanthin yield increases, the canthaxanthin ratio of the precipitate increases and comes close to the composition of the raw precipitate solution (micellized solution). This relationship between the astaxanthin yield and the canthaxanthin ratio does not change even when the solvent concentration is changed and thus does not affect the selectivity. Hence, the precipitation speed can be controlled by appropriately determining the solvent concentration. The solvent concentration, as defined by the volume percentage of the solvent to the volume of the total mixture of water and solvent, is preferably 5% or higher, more preferably 10% or higher and still more preferably 13% or higher, and preferably 50% or lower, more preferably 30% or lower and still more preferably 26% or lower. The precipitation time is generally in the range of 10 minutes to 24 hours, while the solvent concentration and the precipitation time can be determined in consideration of the change in the canthaxanthin ratio in the precipitate with time or the time required for filtration upon separation/collection. In order to adjust the solvent concentration, the volume ratio of water and the extract solution to be spray added may be altered, or the solvent or water may be added for dilution after micellization.

The heating temperature for precipitation (also referred to as precipitation temperature) affects the precipitation speed, where the higher the temperature is, the faster the precipitation speed becomes. In this case, higher precipitation temperature gives higher carotenoid content in the resulting precipitate and thus is advantageous in terms of quality. In addition, higher precipitation temperature gives lower canthaxanthin ratio relative to the astaxanthin yield and thus is advantageous in providing higher selectivity for astaxanthin. The precipitation temperature is preferably 40° C. or higher, more preferably 50° C. or higher and still more preferably 60° C. or higher. The upper limit of the temperature, for example, in the case when ethanol is used, is preferably 80° C. or lower and more preferably 70° C. or lower taking the boiling point into consideration.

The stirring speed upon precipitation affects the precipitation speed, where faster stirring speed increases the precipitation speed. Meanwhile, the carotenoid content in the resulting precipitate does not change and does not affect the quality. Furthermore, the relationship between the astaxanthin yield and the canthaxanthin ratio and thus the selectivity are unaffected by the change in the stirring speed. Therefore, the precipitation speed can also be controlled by the stirring speed. When the speed of stirring is too fast, however, the precipitate may adhere to the stir bar, the stir blade or the wall of the vessel, and can interfere with precipitation/collection. Accordingly, the upper limit of the stirring speed should be determined according to the shape of the vessel or stir blade. Low-speed stirring that allows homogenous stirring within the vessel is preferable in that no adhesion is caused by precipitation.

If it is desirable to prevent oxidation of a carotenoid as much as possible during the micellization or precipitation procedure, it may be treated in an inert gas atmosphere such as nitrogen gas, or an antioxidant used for pharmaceutical products or food may be selected and added to water, the extract solution or the micellized solution (raw precipitate solution). Alternatively, these treatments may be combined together.

The above-mentioned antioxidant is preferably removed from the carotenoid composition at the end but the antioxidant may not necessary be removed depending on the type used (for example, vitamin C).

Moreover, in order to prevent degradation of a carotenoid due to light as much as possible, the micellization or precipitation procedure may be carried out under lightless conditions.

A method for separating and collecting the precipitate after the precipitation procedure is not particularly limited. For example, membrane filtration, centrifugation, decantation or the like may be employed. Since the filtration speed becomes low when the temperature of the filtrate is decreased upon filtration, filtration without cooling is advantageous. Moreover, a step of washing the precipitate with warm water may be added after filtration.

The obtained precipitate is subjected to heating, suspension and stirring using a small amount of ethanol for washing. Ethanol maybe hydrous ethanol, in which case the water content is not particularly limited but preferably 10% or lower. Ethanol is preferably used for about 20-200 times the dry weight of the precipitate but may appropriately be determined according to the purity of the obtained precipitate.

An exemplary method for washing includes a method including the steps of heating to about 75° C., suspending and stirring with heating for an hour, and then cooling and leaching. This procedure may be performed twice or more according to purity.

In this case, impurities other than the carotenoid are dissolved and removed with ethanol, thereby obtaining a highly pure carotenoid. Since cis-astaxanthin is readily soluble in ethanol as compared to trans-astaxanthin, the amount of cis-astaxanthin contained in the resulting carotenoid-containing composition will be reduced while the ratio of trans-astaxanthin will be increased. In the carotenoid-containing composition obtained according to the method of the present invention, the ratio of cis-astaxanthin trans-astaxanthin is 20% or lower, preferably 15% or lower, and still more preferably 10% or lower. Herein, a carotenoid in a free form refers to a state where the hydroxyl group existing in the carotenoid does not form an ester bond with fatty acid. Washing at ambient temperature has less washing effect thr the obtained precipitate while heat washing has higher washing effect.

In order to reduce the amount of the residual solvent, a step of washing by replacing warm water for the solvent may be added at the end of leach washing.

Similarly, in order to prevent oxidation of a carotenoid as much as possible during the heat wash procedure, the treatment can be performed in an inert gas atmosphere such as nitrogen gas, or an antioxidant used for pharmaceutical products or food is selected and added to warm water, the extract solution or the micellized solution (raw precipitate solution). Alternatively, these treatments may be combined together.

The above-mentioned antioxidant is preferably removed from the carotenoid composition at the end but the antioxidant may not necessary be removed depending on the type used (for example, vitamin C).

Moreover, in order to prevent degradation of a carotenoid due to light as much as possible, the heat wash procedure may be carried out under lightless conditions.

The washed precipitate obtained by suspension and stirring with heating is vacuum-dried at 40° C. for 12 hours, and subjected to pulverization/drying to reduce the residual solvent. For example, a procedure of pulverizing in a closed-type mortar grinder (for example, CMT (Tokyo) vibrating mill) under nitrogen replacement conditions for 5 minutes and then vacuum-drying at 40° C. for an hour is performed twice. As compared to concentrated/crystallized crystal by conventional technique, since the carotenoid composition of the present invention is crystallized from the mother liquid containing more water than the solvent, the content of the solvent in the crystal prior to pulverization is smaller. Furthermore, in the step of pulverization/drying, the carotenoid-containing composition is presumed to be forming a loose crystal structure that allows easy removal of the solvent, and thus the residual solvent can readily be reduced by the above-described procedure where the concentration of the residual ethanol becomes 100 ppm or less which is an acceptable level in terms of functionality evaluation. The concentration of the residual ethanol in the carotenoid-containing composition obtained according to the method of the present invention is 200 ppm or less, preferably 150 ppm or less and still more preferably 100 ppm or less.

The carotenoid content and the content of the primary component such as astaxanthin in the carotenoid-containing composition obtained by the above-described production method can be adjusted by appropriately altering the conditions of the purification step so as to give maximum yield. The astaxanthin content in the carotenoid-containing composition of the present invention is defined by the amount of astaxanthin in the carotenoid within the bacterial bodies and the yield of astaxanthin obtained by the subsequent purification step to the pulverization/drying step. When *Paracoccus* bacterium that produces astaxanthin is used as the bacterial body, a carotenoid-containing composition containing astaxanthin for 50% or higher to the amount of total carotenoid in the composition can be obtained. For example, the carotenoid-containing composition of the present invention contains astaxanthin for 40% or higher, preferably 45% or higher and more preferably 50% or higher to the amount of total carotenoid.

As described above, the production method of the present invention is characterized by: dispersing an extract solution of a culture of a carotenoid-producing microorganism extracted with a water-soluble organic solvent in water for micellization; heat stirring at an appropriate solvent concentration for appropriate time for breaking the micelles; preferentially crystallizing/precipitating astaxanthin to reduce canthaxanthin contained in the resulting carotenoid-containing composition; heat washing the precipitate with ethanol; and subjecting the resultant to pulverization/drying. With only these fairly simple procedures, a highly pure carotenoid can be obtained. By preferentially crystallizing/precipitating astaxanthin, canthaxanthin contained in the resulting carotenoid-containing composition can be reduced. The residual solvent can readily be reduced by pulverization/drying as compared to concentrated/crystallized crystal. The content percentage of the carotenoid in the carotenoid-containing composition obtained by the present invention is preferably 85% or higher, more preferably 90% or higher and still more preferably 95% or higher. In addition, the ratio of canthaxanthin to astaxanthin in the carotenoid-containing composition is preferably 2.5% or lower, and more preferably 1.5% or lower.

The method of the present invention is significantly industrially advantageous over conventional techniques in that 1) no complicated procedure is required, and 2) no inefficient purification procedure is required such as making a low concentration solution into a highly pure solution. The present invention is also characterized by being capable of providing an industrial production method that is superior 3) for being capable of providing a highly pure carotenoid composition that contains astaxanthin at a high content at a low cost, 4) for being capable of providing a carotenoid composition having less canthaxanthin content and thus safe as food or a pharmaceutical composition, and 5) for being capable of providing a carotenoid composition having less residual solvent and thus safe and readily processable as food, a pharmaceutical composition or a cosmetic product.

Food, pharmaceutical compositions or cosmetic products containing the carotenoid-containing composition of the present invention are also encompassed in the present invention. Dosage forms of pharmaceutical products comprising a highly pure carotenoid containing astaxanthin at a high content produced by a production method according to the present invention include powder, granule, pill, soft capsule, hard capsule, tablet, chewable tablet, disintegrating tablet, syrup, liquid medicine, suspension, suppository, ointment, cream, gel, sticky medicine, inhalant, injection and the like. These formulations are prepared in accordance with a general method. Since a carotenoid is hardly soluble in water, it is dissolved in a non-hydrophilic organic solvent such as a vegetable oil, an animal oil or the like; dispersed or emulsified in an aqueous solution with an emulsifier, a dispersant, a surfactant or the like using a homogenizer (high pressure homogenizer); or dissolved by increasing the temperature. In order to improve carotenoid absorption, a carotenoid may be used after being pulverized to an average particle diameter as small as about 1 micrometer.

Additives usable for producing the formulations include, for example, animal and vegetable oils including soybean oil, safflower oil, olive oil, germ oil, sunflower oil, grapeseed oil, beef tallow, sardine oil and the like; polyhydric alcohols including polyethylene glycol, propylene glycol, glycerin, sorbitol and the like; surfactants including sorbitan fatty acid ester, sucrose fatty acid ester, glycerin fatty acid ester, polyglycerin fatty acid ester and the like; excipients including purified water, lactose, starch, crystalline cellulose, D-mannitol, lecithin, gum arabic, sorbitol solution, sugar solution and the like; sweeteners; coloring agents; pH adjusters; flavor substances; etc. A liquid formulation may be dissolved or suspended in water or any other appropriate medium upon administration. A tablet or granule may be coated by a well known method or encapsulated with a sol-like or gel-like substance.

Administration by injection is preferably performed intravenously, intraperitoneally, intramuscularly, subcutaneously, percutaneously, intra-articularly, in synovial bursa, in bulla, in periosteum, sublingually, in oral cavity or the like, and particularly preferably performed intravenously or intraperitoneally. The intravenous administration may be either drip administration or bolus administration.

When a carotenoid is used as a pharmaceutical product, a usage or a dosage for an adult (weight 60 kg) is 1 mg to 3 g, preferably 3 mg to 1 g, and more preferably 10 mg to 670 mg per day. In conversion into 1 kg of the adult body weight per day, the dosages are 17 μg to 50 mg, 50 μg to 17 mg, and 160 μg to 12 mg, respectively. Such a dosage is administered once or in several doses a day. The pharmaceutically effective amount, administration method, administration means and administration period can be appropriately set by a person of ordinary skill in the art in accordance with the clinical state, sex, age, body weight or the like of the subject of administration.

Food forms comprising a highly pure carotenoid containing astaxanthin at a high content according to the present invention include, for example, supplements (powder, granule, soft capsule, hard capsule, tablet, chewable tablet, fast-disintegrating tablet, syrup, liquid medicine, etc.), drinks (tea, carbonated drink, lactic drink, sports drink, etc.), confectionaries (gummi, jelly, chewing gum, chocolate, cookie, candy, etc.), oils, fat and oil foods (mayonnaise, dressing, butter, cream, margarine, etc.), seasonings (ketchup, sauce, etc.), fluid diet, dairy products (milk, yogurt, cheese, etc.), breads, noodles (udon, soba, ramen, pasta, fried noodle, kishimen, somen, hiyamugi, bihon, etc.), and the like. The form of food, however, is not limited to these examples.

Functional food comprising a highly pure carotenoid containing astaxanthin at a high content according to the present invention may optionally contain any of various nutrients, various vitamins (vitamin A, vitamin B1, vitamin B2, vitamin B6, vitamin B12, vitamin C, vitamin E, etc.), various minerals, dietary fiber, polyunsaturated fatty acid, other nutrients (coenzyme Q10, carnitine, sesamine, α-lipoic acid, inositol, D-chiro inositol, pinitol, phosphatidylserine, phosphatidyl DHA, phosphatidyl inositol, taurine, glucosamine, chondroitin sulfate, S-adnosylmethionine etc.), stabilizers such as dispersants and emulsifiers, sweeteners, taste enriching components (citric acid, malic acid, etc.), flavor substances, royal jelly, propolis, agaricus, and the like. Herbs such as peppermint, bergamot, chamomile, lavender, thyme and the like can also be blended with the food of the invention. Elements such as theanine, dehydroepiandosteron, melatonin and the like can also be blended with the food of the present invention.

Cosmetic products comprising a highly pure carotenoid containing astaxanthin at a high content according to the present invention include cream, emulsion, lotion, microemulsion essence, bathwater additive and the like, and may contain aromatic essence or the like.

When a carotenoid is used as food or a supplement, there is no specific limitation to the usage and dosage. The dosage may be 17 μg to 50 mg, preferably 54 μg, to 17 mg and more preferably 160 μg to 12 mg per 1 kg of the adult body weight (weight 60 kg).

When a carotenoid is used as a cosmetic product, the blended amount may be 10 μg to 5 g, preferably 10 μg to 2 g and more preferably 10 μg to 1 g per 100 g of the cosmetic product.

EXAMPLES

The present invention will be described by way of examples, a reference example, formulation examples and test examples. The scope of the present invention is not limited, to the following examples.

Astaxanthin, canthaxanthin and a carotenoid were quantified in the examples by high performance liquid chromatography (HPLC). Two of Wakosil-II SIL-100 (φ4.6×250 mm) columns (produced by Wako Pure Chemical Industries, Ltd.) were connected to each other to be used as a column. Elution was performed by running an n-hexane-tetrahydrofuran-methanol mixture solution (40:20:1) as a mobile phase, at a flow rate of 1.0 ml/min. at a constant temperature around room temperature. For measurement, the sample dissolved in tetrahydrofuran was 100-fold diluted with the mobile phase. Twenty μL of the resultant solution was loaded and the column elution solution was detected at a wavelength of 470 nm. As a standard product for quantification, astaxanthin produced by Sigma (Cat. No. A9335) was used. The astaxanthin concentration of the standard solution was determined using the following formula after measuring the absorbance of the standard solution at 477 nm (A) and the area percentage % (B) of the astaxanthin peak upon HPLC analysis under the above-described conditions.

$$\text{Astaxanthin concentration(mg/L)} = A/2150 \times B \times 100$$

A ratio analysis of cis-astaxanthin and trans-astaxanthin in the examples was conducted by employing high-performance chromatography (HPLC). TSKgel 80Ts column (φ4.6×150 mm) (Tosoh) was used. Elution was carried out by running a mobile phase, i.e., a methanol-water mixture solution (95:5) (A) and THF (B), at the following linear gradient composition at 35° C. at 1.0 ml/minute. The gradient composition was as follows: A/B=100/0 (0 minute), A/B=100/0 (5 minutes), A/B=20/80 (25 minutes), A/B=20/80 (29 minutes), A/B=100/0 (30 minutes) and A/B=100/0 (45 minutes).

For measurement, 5 μl of a solution obtained by dissolving the sample with tetrahydrofuran was loaded and the column eluent was detected at a wavelength of 470 nm. Moreover, as a standard product, a mixture solution of cis-astaxanthin and trans-astaxanthin obtained by dissolving astaxanthin from Sigma (Cat. No. A9335) and the sample in chloroform followed by heating was used.

The residual ethanol in each example was analyzed by using headspace gas chromatography (HS-GC), HS-40 (PerkinElmer) was used as the headspace device. A sample prior to pulverization that weighed 10 mg and a sample after pulverization/drying that weighed 50 mg were each packed into a 22-ml volume HS vial together with 10 ml chlorobenzene and placed in the HS device. The samples were dissolved by heating at 105° C. for 60 minutes to liberate ethanol contained in the dissolved solution and then gas phase moieties were loaded for analysis. ZB-624 (0.32 mm I.D.×30 m, df=1.80 μm) (Phenomenex) was used as the GC column, nitrogen was used as the carrier gas, the flow rate was 4 ml/min, the temperature at the loading site was 140° C., the temperature at the detection site was 250° C., and FID detector was used. The temperature of the column was maintained at 40° C. for 5 minutes after the initiation of analysis, raised to 170° C. by spending 3.25 minutes, maintained at 170° C. for 5 minutes and back to 40° C. A standard sample for quantitation was obtained by dissolving ethanol into chlorobenzene at 0.1 ppm, 1 ppm and 10 ppm and packing 10 ml each of them into specifically-designed vials.

Example 1

Production of Highly Pure Carotenoid Having High Astaxanthin Content (1)

Step 1: Step of Extraction with Ethanol

Five-hundred ml of ethanol was added to 25 g of dry bacterial bodies that were obtained by culturing E-396 strain (FERM BP-4283) and that contained 20 mg of astaxanthin and 0.72 mg of canthaxanthin per gram thereof, and stirred in a nitrogen-replaced atmosphere at 95° C. for 2 minutes in a high-pressure vessel to extract a carotenoid that contains astaxanthin. After cooling to 50° C., the bacterial bodies were removed by filtration, and the bacterial body cake was further washed with ethanol, thereby obtaining 589 ml of an extract solution having an astaxanthin concentration of 668 μg/ml, a canthaxanthin concentration of 24 μg/ml, a carotenoid concentration of 1370 μg/ml and canthaxanthin/astaxanthin ratio of 3.53%.

Step 2: Steps of Micellization and Precipitation 589 ml of the extract solution obtained by Step 1 of the present example was sprayed onto 2,590 ml of warm water at 65° C. for 10 minutes using a 200 ml injector while stirring at 350 rpm to disperse for micellization. The concentration of ethanol at this point was 18.7%. The resultant was sealed and continuously kept warm at 65° C. while stirring at 150 rpm for 3.5 hours to preferentially precipitate astaxanthin. Then, the precipitate was leached without cooling. At the end of leaching, 100 ml of warm water at 65° C. was added onto the precipitate cake for washing. The canthaxanthin/astaxanthin ratio of the precipitate was 1.46%.

Meanwhile, the precipitate was sampled during the precipitation and subjected to leaching for analysis. The canthaxanthin/astaxanthin ratio of the precipitate with time was observed 0.72% after 2 hours, 0.97% after 2.5 hours and 1.20% after 3 hours.

Step 3: Steps of Precipitation and Heat Washing

The precipitate obtained by Step 2 of the present example was suspended in 70 ml of ethanol, washed by heat stirring at a product temperature of 75° C. for an hour and then cooled to room temperature. Then, the precipitate was leached. At the end of leaching, 5 ml of ethanol and subsequently 5 ml of warm water at 65° C. were added for washing. The resultant was vacuum-dried at 40° C. for 12 hours, thereby obtaining 350 mg of a dry product. The astaxanthin content in this dry product was 71.6%, the carotenoid content was 99.8%, the canthaxanthin/astaxanthin ratio was 1.46%, the cis-astaxanthin/trans-astaxanthin ratio was 2.84%, and the ethanol content was 3,240 ppm (w/w).

Step 4: Step of Pulverization/Drying

The dry product obtained by Step 3 of the present example was pulverized in a closed-type mortar grinder (CMT (Tokyo) vibrating mill) under nitrogen replacement conditions for 5 minutes and vacuum-dried at 40° C. for an hour. This procedure was performed twice. The astaxanthin content of this dry pulverized product was 71.5%, the carotenoid content was 98.9%, the canthaxanthin/astaxanthin ratio was 1.44%, the cis-astaxanthin/trans-astaxanthin ratio was 4.80%, and the ethanol content was 40.3 ppm (w/w).

Pulverization/drying was found to greatly reduce the ethanol content. Although the cis-astaxanthin/trans-astaxanthin ratio slightly increases at this point, there is no significant change in the astaxanthin content, the carotenoid content and the canthaxanthin/astaxanthin ratio.

Reference Example 1

Influence of Carrying Out Precipitation Washing at Room Temperature

Steps 1 to 3 were carried out in the same manner as in Example 1 except washing was performed at room temperature instead of precipitation and heat washing. As a result, the astaxanthin content in the resulting dry product was 53.5%, the carotenoid content was 80.5%, the canthaxanthin/astaxanthin ratio was 1.46%, the cis-astaxanthin/trans-astaxanthin ratio was 12.3% and the ethanol content was 119 ppm (w/w).

As a result of washing at room temperature, the astaxanthin content and the carotenoid content were lower than those in the case of heat washing, showing that washing was poorly effective in removing impurities. In addition, the cis-astaxanthin/trans-astaxanthin ratio was high, showing that the effect of removing cis-astaxanthin was also low.

Example 2

Production of Highly Pure Carotenoid Having High Astaxanthin Content (2)

Step 1: Step of Extraction with Ethanol

Five-hundred ml of 90% (v/v) ethanol was added to 25 g of dry bacterial bodies that were obtained by culturing E-396 strain (FERM BP-4283) and that contained 20 mg of astaxanthin and 0.72 mg of canthaxanthin per gram thereof, and stirred in a nitrogen-replaced atmosphere at 100° C. for 2 minutes in a high-pressure vessel to extract a carotenoid that contains astaxanthin. After cooling to 50° C., the bacterial bodies were removed by filtration, and the bacterial body cake was further washed with 90% (v/v) ethanol, thereby obtaining 568 ml of an extract solution having an astaxanthin concentration of 605 μg/ml, a canthaxanthin concentration of 20 μg/ml, a carotenoid concentration of 1,210 μg/ml and a canthaxanthin/astaxanthin ratio of 3.32%, Step 2: Steps of Micellization and Precipitation 568 ml of the extract solution obtained by Step 1 of the present example was sprayed onto 2,180 ml of warm water at 65° C. for 10 minutes using a 200 ml injector while stirring at 350 rpm to disperse for micellization. The concentration of ethanol at this point was 18.7%. The resultant was sealed and continuously kept warm at 65° C. while stirring at 150 rpm for 5.4 hours to preferentially precipitate astaxanthin. Then, the precipitate was leached without cooling. At the end of leaching, 100 ml of warm water at 65° C. was added onto the precipitate cake for washing. The canthaxanthin/astaxanthin ratio of the precipitate was 1.44%.

Meanwhile, the precipitate was sampled during the precipitation and subjected the precipitate to leaching for analysis. The canthaxanthin/astaxanthin ratios of the precipitate with time was observed 0.53% after 2 hours, 0.76% after 3 hours, 1.04% after 4 hours and 1.34% after 5 hours.

Step 3: Steps of Precipitation and Heat Washing

The precipitate obtained by Step 2 of the present example was suspended in 70 ml of 90% (v/v) ethanol, washed by heat stirring at a product temperature of 75° C. for an hour and then cooled to room temperature. Then, the precipitate was leached. At the end of leaching, 5 ml of 90% (v/v) ethanol and subsequently 5 ml of warm water at 65° C. were added for washing. The resultant was vacuum-dried at 40° C. for 12 hours, thereby obtaining 264 mg of a dry product. The astaxanthin content in this dry product was 70.2%, the carotenoid content was 99.1%, the canthaxanthin/astaxanthin ratio was 1.49%, the cis-astaxanthin/trans-astaxanthin ratio was 4.93% and the ethanol content was 1,810 ppm (w/w).

Step 4: Step of Pulverization/Drying

The dry product obtained by Step 3 of the present example was pulverized in a closed-type mortar grinder (CMT (Tokyo) vibrating mill) under nitrogen replacement conditions for 5 minutes and vacuum-dried at 40° C. thr an hour. This procedure was performed twice. The astaxanthin content of this dry pulverized product was 69.1%, the carotenoid content was 98.3%, the canthaxanthin/astaxanthin ratio was 1.48%, the cis-astaxanthin/trans-astaxanthin ratio was 6.08% and the ethanol content was 612 ppm (w/w).

A dry pulverized product having equivalent quality to that in Example 1 can be obtained even when 90% (v/v) ethanol is used as an extraction solvent and as a solvent for precipitation/heat washing.

[Exemplary Food 1] Margarine

The astaxanthin composition obtained in Example 1 was added as an antioxidant and a coloring agent to vegetable oil such that the astaxanthin composition would be contained at 5% by weight of margarine. The resultant substance was stirred together with an emulsifier and the like so as to be homologous to produce margarine by a general method. As compared with usual margarine, the obtained margarine exhibited a pale red color because of the presence of astaxanthin.

[Exemplary Food 2] Olive Oil

The astaxanthin composition obtained in Example 1 was added to account 0.25 weight % of the olive oil, stirred and dissolved at 50° C. and cooled to ambient temperature. This olive oil exhibited darker red color as compared to general olive oil due to the presence of astaxanthin. The color tone was able to be altered by changing the amount of the astaxanthin composition added. Moreover, astaxanthin that was once dissolved did not precipitate even when it was left for prolonged time.

[Exemplary Formulation 1] Astaxanthin-Containing Tablet

To 110 parts by weight of the carotenoid-containing composition obtained in Example 1, 330 parts by weight of crystalline cellulose, 15 parts by weight of carmellose-calcium, 10 parts by weight of hydroxypropyl cellulose and 60 parts by weight of purified water were blended and dried by a general method. Then, 10 parts by weight of magnesium stearate was added, and the resultant substance was tableted to obtain tablets for 100 mg containing 20 mg of the carotenoid-containing composition per tablet.

[Exemplary Formulation 2] Astaxanthin-Containing Soft Capsule

One part by weight of the carotenoid-containing composition obtained in Example 1 was suspended in 5-fold part by weight of soybean oil, and the resultant substance was sufficiently mixed so as to be homologous. Then, the resultant substance was filled into capsules with a capsule filler to obtain reddish brown capsules of about 300 mg content.

[Exemplary Cosmetic Product 1] Astaxanthin-Containing Cream (Cosmetic Product)

The astaxanthin-containing composition obtained in Example 1 was added to white petrolatum to 10% by weight, and dispersed with an aromatic substance and the like so as to be homologous to produce a cream agent by a general method.

INDUSTRIAL APPLICABILITY

The present invention can provide a composition containing a high content of a highly pure, low-cost and safe carotenoid derived from natural products, and a method for industrially producing the same. Accordingly, the present invention can also provide functional food, a pharmaceutical composition and a cosmetic product comprising such a composition.

Accession Number

E-396 strain has been deposited as international deposition to the International Patent Organism Depositary, the National Institute of Advanced Industrial Science and Technology as follows:

International Deposition Authority: International Patent Organism Depositary

National Institute of Advanced Industrial Science and Technology (former National institute of Bioscience and Human-Technology, Agency of Industrial Science and Technology, Ministry of International Trade and Industry)

Central 6, Higashi 1-1-1, Tsukuba-shi, Ibaraki-ken, 305-8566

Identification Indication: E-396

Accession No: FERM BP-4283

Date of original deposition: Apr. 27, 1993

Sequence Listing Free Text

SEQ ID NO:1: Descriptions on unknown organism (E-396)

The invention claimed is:

1. A method for producing an astaxanthin containing composition comprising:
   1) subjecting a culture of *Paracoccus* to an extraction treatment using a water-soluble organic solvent to obtain a resulting solution;
   2) spraying the resulting solution onto water to disperse for micellization to produce a resulting micellized solution; and
   3) heat stirring the resulting micellized solution in a solvent to break the micelles and precipitate the astaxanthin from the solution to produce the astaxanthin containing composition.

2. The method according to claim 1 further comprising:
   4) collecting and heat washing the astaxanthin containing composition with ethanol; and
   5) further subjecting the astaxanthin containing composition to pulverization/drying.

3. The method according to claim 1 wherein the water-soluble organic solvent is ethanol.

4. The method according to claim 1 wherein the astaxanthin containing composition is a composition having a carotenoid content of 85% or higher.

5. The method according to claim 1 wherein the ratio of astaxanthin to the carotenoid contained in the astaxanthin containing composition is 40% or higher.

6. The method according to claim 1 wherein the ratio of canthaxanthin to astaxanthin contained in the astaxanthin containing composition is 2.5% or lower.

7. The method according to claim 1 wherein the ratio of cis-astaxanthin to trans-astaxanthin contained in the astaxanthin containing composition is 20% or lower.

8. The method according to claim 1 wherein ethanol content in the astaxanthin containing composition is 200 ppm or less.

9. The method according to claim 1 wherein the *Paracoccus* is E-396 strain (FERM BP-4283).

* * * * *

UNITED STATES PATENT AND TRADEMARK OFFICE
CERTIFICATE OF CORRECTION

PATENT NO.        : 8,524,289 B2
APPLICATION NO.   : 13/203324
DATED             : September 3, 2013
INVENTOR(S)       : Shimizu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 106 days.

Signed and Sealed this

Fifteenth Day of September, 2015

Michelle K. Lee
*Director of the United States Patent and Trademark Office*